(12) United States Patent
Traulsen et al.

(10) Patent No.: US 8,043,744 B2
(45) Date of Patent: Oct. 25, 2011

(54) BATTERY OPERATED DEVICE, IN PARTICULAR IMPLANTABLE MEDICAL-ELECTRONIC DEVICE

(75) Inventors: Tim Traulsen, Pirna (DE); Juergen Drews, Pirna (DE); Thomas Hucke, Dresden (DE)

(73) Assignee: Biotronik CRM Patent AG, Baar (CH)

( * ) Notice: Subject to any disclaimer, the term of this patent is extended or adjusted under 35 U.S.C. 154(b) by 596 days.

(21) Appl. No.: 12/198,708

(22) Filed: Aug. 26, 2008

(65) Prior Publication Data

US 2009/0075167 A1 Mar. 19, 2009

(30) Foreign Application Priority Data

Sep. 13, 2007 (DE) .................... 10 2007 043 660

(51) Int. Cl.
*H01M 2/08* (2006.01)
*H01M 6/16* (2006.01)
*H01M 2/02* (2006.01)
*H01M 4/50* (2010.01)

(52) U.S. Cl. .................... 429/199; 429/176; 429/224

(58) Field of Classification Search .................... None
See application file for complete search history.

(56) References Cited

U.S. PATENT DOCUMENTS

| | | |
|---|---|---|
| 6,273,904 B1 | 8/2001 | Chen |
| 2005/0003269 A1 | 1/2005 | Nanjundaswamy et al. |
| 2005/0186481 A1* | 8/2005 | Ogawa et al. ............... 429/332 |
| 2006/0035137 A1 | 2/2006 | Maruo et al. |
| 2006/0068281 A1 | 3/2006 | Hiratsuka et al. |
| 2006/0147795 A1* | 7/2006 | Li et al. ............... 429/209 |
| 2007/0065726 A1 | 3/2007 | Yumoto et al. |
| 2007/0077496 A1* | 4/2007 | Scott et al. ............... 429/326 |
| 2008/0039634 A1* | 2/2008 | Matsunaga et al. ........ 548/300.4 |

FOREIGN PATENT DOCUMENTS

| | | |
|---|---|---|
| DE | 19544909 | 6/1996 |
| EP | 1181952 | 2/2002 |
| EP | 1832311 | 9/2007 |
| WO | 2006/050098 | 5/2006 |

OTHER PUBLICATIONS

European Search Report, dated Oct. 6, 2008, 5 pages.
German Search Report, dated Jul. 9, 2008, 2 pages.
Boon, J.A.; Levisky, J.A.; Pflug, J.L.; Wilkes, J.S.; J. Org. Chemistry, 1986, 51, 480-483.
Fry, S.E.; Pienta, J.N.; J. Am. Chem. Society, 1985, 107, 6399-6400.
H. Tokuda et al: "Physicochemical Properties and Structures of Room Temperature Ionic Liquids. 1. Variation of Anionic Species", J. Phys. Chem. B 2004, 108, 16593.

* cited by examiner

*Primary Examiner* — John S Maples
(74) *Attorney, Agent, or Firm* — ARC IP Law, PC; Joseph J. Mayo

(57) ABSTRACT

Battery-operated device, having an electrically operated functional unit and an electrochemical voltage source, which are housed together in an essentially gas-tight device housing, the electrochemical voltage source having an electrolyte based on an ionic liquid and a coating-free plastic battery housing.

2 Claims, 2 Drawing Sheets

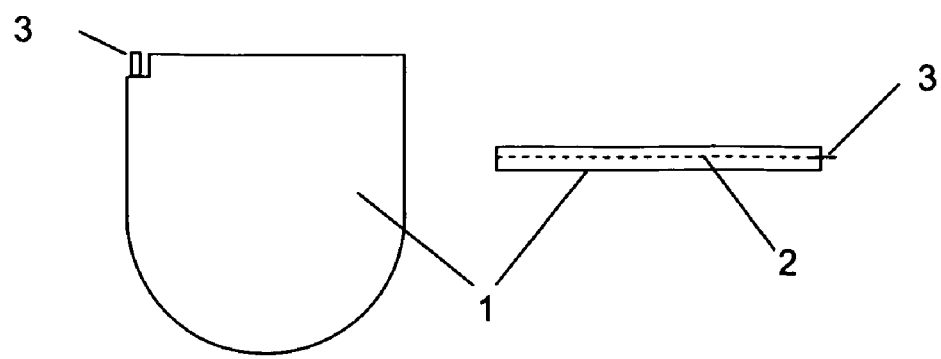
FIG. 1A   FIG. 1B
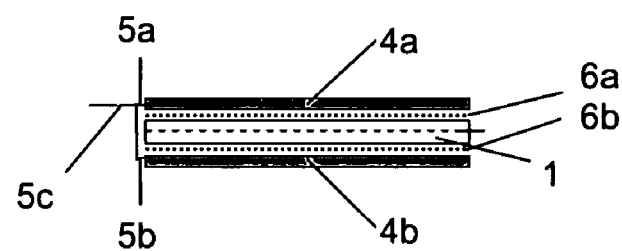
FIG. 2
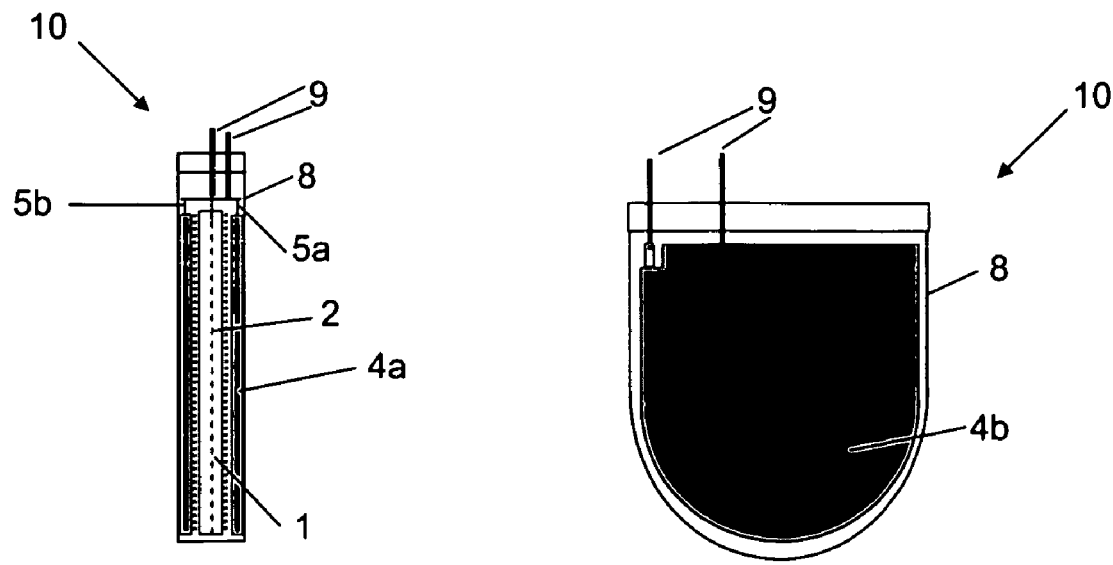
FIG. 3A   FIG. 3B

BATTERY OPERATED DEVICE, IN PARTICULAR IMPLANTABLE MEDICAL-ELECTRONIC DEVICE

This application takes priority from German Patent Application DE 10 2007 043 660.4, filed 13 Sep. 2007, the specification of which is hereby incorporated herein by reference.

BACKGROUND OF THE INVENTION

1. Field of the Invention

The invention relates to a battery operated device having an electrically operated functional unit and an electrochemical voltage source, which are housed together in an essentially gas-tight device housing, in particular an implantable medical-electronic device having such a basic construction.

2. Description of the Related Art

Devices of this type, especially also implantable medical-electronic devices, such as cardiac pacemakers, implantable defibrillators, neurostimulators, or implantable insulin or medication pumps, etc., are known in a great manifold of designs. They currently usually contain a lithium ion secondary element (also referred to in short as a "lithium battery" hereafter) as the power source, which has a gas-tight welded metal housing, normally made of stainless steel or titanium.

For such batteries, this complex housing is a significant cost factor, because of which a simpler solution has been sought for some time for reasons of cost. Plastic housings are fundamentally to be taken into consideration for this purpose, because of the easy producibility and extraordinarily low costs.

The use of batteries—especially lithium batteries—having housings made of plastic has not been possible until now for medical implants, because typically liquid or gel electrolytes based on organic solvents or solvent mixtures are used in lithium batteries. Organic carbonates, ethers, or esters are preferably used. Organic polymers are permeable to vapors of the solvents—above all at elevated temperatures—so that if a plastic housing is used in a gas-tight sealed implant, solvent may reach the inner chamber of the implant. This solvent may react with other components of the implant, such as electronic components or insulation, and trigger malfunctions or defects.

BRIEF SUMMARY OF THE INVENTION

It is the object of the invention to provide a device of the type characterized at the beginning which avoids this fundamental obstacle using a suitable combination of design features and material aspects and is more cost-effectively producible in this way.

This object is achieved by a device having the features as claimed herein. Expedient refinements of the idea of the invention are the subject matter of the dependent claims.

The invention includes the fundamental idea of using an electrolyte based on an ionic liquid in the electrochemical voltage source of the device.

Ionic liquids are liquids which exclusively contain ions. These are thus liquid salts, without the salt being dissolved in a solvent. For some time, hot molten salts (for table salt above 800° C.) were the only known examples of liquids of this type. Currently, ionic liquids are predominantly referred to in connection with salts which are already liquid at temperatures below 100° C.

Examples of cations used are alkylated imidazolium, pyridinium, ammonium, or phosphonium ions. Greatly varying ions from the simple halogenide via more complex inorganic ions such as tetrafluoroborates up to large organic ions such as trifluoromethane sulfonimide are used as the anions. The size of the participating ions obstructs the formation of a strong crystal lattice. Little thermal energy is therefore already sufficient to overcome the lattice energy and break up the solid crystal structure.

Ionic liquids are distinguished by an array of interesting properties: they are thermally stable, nonflammable, have an extremely low, hardly measurable vapor pressure, and have very good solution properties for polar substances and salts. In addition, because of their purely ionic structure, they also have interesting electrochemical properties, such as electrical conductivity which is often also accompanied by high electrochemical stability (i.e., to oxidations and reductions). For example, the solubility in water or organic solvents may be determined largely freely by variation of the side chains of the cation and the selection of suitable anions.

The first publications about their use as catalysts (Boon, J. A.; Levisky, J. A.; Pflug, J. L.; Wilkes, J. S.; J. Org. Chemistry, 1986, 51, 480-483) and as solvents (Fry, S. E.; Pienta, J. N.; J. Am. Chem. Society, 1985, 107, 6399-6400) for organic reactions were published at the end of the 80s. More recently, suggestions have also become known for using ionic liquids as novel electrolytes in electrochemical devices, such as lithium secondary elements, double-layer capacitors, fuel cells, etc.; compare H. Tokuda et al: "Physicochemical Properties and Structures of Room Temperature Ionic Liquids. 1. Variation of Anionic Species", J. Phys. Chem. B 2004, 108, 16593, in this regard, as well as further citations in this publication.

Lithium salts may be dissolved in ionic liquids. These solutions may be used as electrolytes in lithium batteries. Electrolytes based on ionic liquids have no vapor pressure and thus also no permeability through a plurality of polymer substances, i.e., the electrolyte may not penetrate a battery housing made of plastic.

The invention, especially also the use of plastic battery housings (in other words: battery housings made of organic polymers), has the following advantages:

low weight
simple processing
low costs
manifold possibilities in the shaping
large selection of materials.

When reference is made hereafter to a plastic battery housing, this expressly includes the use of composite materials, such as plastic/ceramic composites, or other housing variants, whose main component is plastic or such a composite material.

According to the above statement, it is provided in particular in the invention that the electrolyte is in a grade free of solvents and the plastic housing is implemented in such a way that no measurable outgassing from the battery housing occurs at operating temperature. In particular, this allows an implementation of the device as an implantable medical-electronic device, in particular a cardiac pacemaker, defibrillator, insulin or medication pump, or the like, having gas-tight welded or sealed metal device housing.

The entry of water vapor into the device interior and thus also into the interior of the electrochemical element (through the plastic battery housing, which is permeable to water vapor) is prevented by the gas-tight external housing. Damage to water-sensitive components such as a lithium battery by entering water vapor is reliably prevented in this way. This allows an additional coating of the plastic housing to achieve a water vapor barrier which encloses the battery component to be dispensed with, which saves costs.

In cost-effective implementations of the invention using established mass production technologies of plastic processing, it is provided that the battery housing has an injection-molded part or a film deep-drawn part.

According to a first variant, the electrochemical element is a liquid electrolyte and has a battery housing implemented as liquid-tight, in particular having welded-on cover. An alternative embodiment thereto provides that the electrochemical element has a gel electrolyte and a battery housing not implemented as liquid-tight, in particular having a simple formfitting inserted cover. Cost-effective mass plastics such as polyethylene or polycarbonate may be used without problems as materials for the battery housing.

In regard to the selection of suitable ionic liquids which have a liquid or gel-type state at body temperature of a human or mammal, it is provided that the ionic liquid forming the base of the electrolyte has alkylated imidazolium, pyridinium, ammonium, or phosphonium ions as cations. Typical anode and cathode materials of common electrochemical elements—in particular of a lithium battery—are usable in the context of the invention. In this regard, it is thus provided that the electrochemical element has at least one material from the group manganese dioxide, copper oxyphosphate, lithium iron phosphate, lithium cobalt oxide, lithium nickel cobalt oxide, carbon monofluoride, silver vanadium oxide, and copper oxide as the cathode material and/or a material from the group lithium, carbon, and lithium titanium oxide as the anode material.

BRIEF DESCRIPTION OF THE DRAWINGS

Advantages and expedient features of the invention also result from the following description of an exemplary embodiment on the basis of the figures. In the figures:

FIGS. 1A and 1B show a top view and a side view, respectively, of the cathode of the lithium battery of a device according to an exemplary embodiment of the invention, FIG. 2 shows a side view of the complete electric configuration of the lithium battery according to FIG. 1, FIGS. 3A and 3B show a schematic top view and side view, respectively, of the complete lithium battery according to this exemplary embodiment.

DETAILED DESCRIPTION OF THE INVENTION

Figure 4:
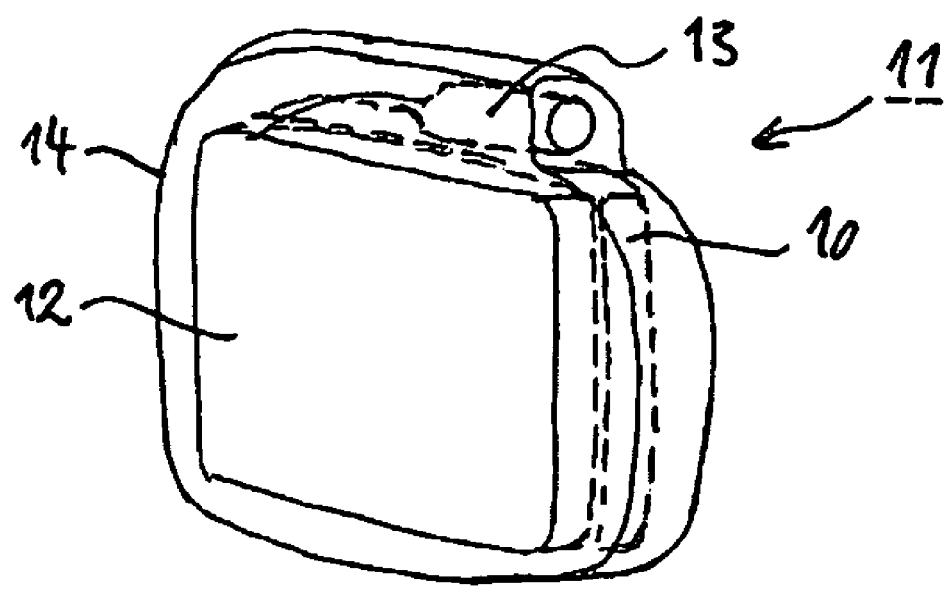
FIG. 4 shows a schematic sketch (as a perspective illustration) of a cardiac pacemaker as an exemplary embodiment of the device according to the invention.

According to the exemplary embodiment, 91% manganese oxide is mixed homogeneously with 7% expanded graphite and 2% of a PTFE powder. This mixture is compressed into an approximately 3.5 mm thick electrode 1 having a centrally situated discharge lattice 2.

The discharge lattice is provided with a contact tab 3, with the aid of which the cathode may be contacted at a housing feedthrough. The total surface of the electrode is approximately 10 cm$^2$. The electrode is dried at a temperature of 270° C.-300° C. and a pressure of $10^{-3}$ mbar for at least 1 h.

The electrode is subsequently provided on both sides with identically-shaped lithium anodes 4a and 4b. These also have contact tabs 5a and 5b, using which the anodes may be contacted at a housing feedthrough 5c. Microporous diaphragms made of a polyolefin or a ceramic material are used as the separators 6a and 6b.

This construction is welded into a battery housing 8 made of plastic, e.g., made of polyethylene or polycarbonate, having a wall thickness of 0.2 mm. The electrodes of the battery are led outward through contact pins 9 embedded in the plastic covers, so that a lithium battery 10 results as a whole.

The battery is subsequently filled with a 0.7 M solution of lithium perchlorate in triethylsulfonium bis(trifluoromethylsulfonyl)imide and then welded.

FIG. 4 schematically shows a cardiac pacemaker 11 as an exemplary embodiment of a device according to the invention, which, in addition to the lithium battery 10 shown in FIGS. 3A and 3B, has an electronics block 12 supplied with current thereby and an electrode line connector 13 connected thereto in a gas-tight welded titanium housing 14.

The implementation of the invention is not restricted to this example, but rather is also possible in a plurality of alterations which are within the context of normal measures of those skilled in the art.

What is claimed is:

1. A battery-operated device (11), having
an electrically operated functional unit (12) and an electrochemical voltage source (10), which are housed together in an essentially gas-tight device housing (14); and,
wherein the electrochemical voltage source has
an electrode comprising 91% manganese oxide, 7% expanded graphite and 2% PTFE powder,
an electrolyte based on an ionic liquid comprising lithium perchlorate in triethylsulfonium bis(trifluoromethylsulfonyl)imide wherein said electrolyte is free of solvents,
a coating-free plastic battery housing (8) comprising polyethylene or polycarbonate that is configured to prevent outgassing from the coating-free plastic battery housing at operating temperature.

2. The device according to claim 1, wherein said battery-operated device is an implantable medical-electronic device, a cardiac pacemaker, defibrillator, neurostimulator, insulin or medication pump having a gas-tight welded or sealed metal device housing.

* * * * *